US009622478B2

(12) United States Patent
Vardi et al.

(10) Patent No.: US 9,622,478 B2
(45) Date of Patent: Apr. 18, 2017

(54) TOPICAL FORMULATIONS FOR TREATING PARASITIC INFESTATIONS

(71) Applicant: SOLANO S.P. LTD., Ram On (IL)

(72) Inventors: Amnon Vardi, Ram On (IL); Nimrod Vardi, Ram On (IL); Fabian Trumper, Afula (IL)

(73) Assignee: SOLANO S.P. LTD., Ram On (IL)

( * ) Notice: Subject to any disclaimer, the term of this patent is extended or adjusted under 35 U.S.C. 154(b) by 0 days.

(21) Appl. No.: 14/435,455

(22) PCT Filed: Oct. 16, 2013

(86) PCT No.: PCT/IB2013/059385
§ 371 (c)(1),
(2) Date: Apr. 14, 2015

(87) PCT Pub. No.: WO2014/060960
PCT Pub. Date: Apr. 24, 2014

(65) Prior Publication Data
US 2015/0257388 A1 Sep. 17, 2015

Related U.S. Application Data

(60) Provisional application No. 61/714,242, filed on Oct. 16, 2012, provisional application No. 61/841,429, filed on Jul. 1, 2013.

(51) Int. Cl.
| A01N 43/30 | (2006.01) |
| A61K 31/36 | (2006.01) |
| A01N 53/00 | (2006.01) |
| A01N 51/00 | (2006.01) |
| A01N 33/08 | (2006.01) |

(52) U.S. Cl.
CPC ............ *A01N 53/00* (2013.01); *A01N 33/08* (2013.01); *A01N 43/30* (2013.01); *A01N 51/00* (2013.01)

(58) Field of Classification Search
CPC .... A01N 53/00; A01N 2300/00; A01N 43/30; A01N 51/00; A01N 33/08
See application file for complete search history.

(56) References Cited

U.S. PATENT DOCUMENTS

| 4,933,371 | A | * | 6/1990 | Hink ...................... A01N 49/00 514/739 |
| 5,660,844 | A | | 8/1997 | Christie et al. |
| 5,968,990 | A | | 10/1999 | Jon et al. |
| 6,024,972 | A | | 2/2000 | Narayanan et al. |
| 6,255,350 | B1 | | 7/2001 | Jon et al. |
| 6,337,345 | B1 | | 1/2002 | Fukuchi |
| 6,372,242 | B1 | | 4/2002 | Gutierrez |
| 6,543,389 | B2 | | 4/2003 | Hedde |
| 6,588,374 | B1 | | 7/2003 | Cottrell et al. |
| 6,740,653 | B2 | | 5/2004 | Narayanan et al. |
| 6,814,030 | B2 | | 11/2004 | Cottrell et al. |
| 6,835,386 | B2 | | 12/2004 | Gutierrez |
| 6,867,223 | B2 | | 3/2005 | Cottrell et al. |
| 6,889,632 | B2 | | 5/2005 | Cottrell et al. |
| 6,984,662 | B2 | | 1/2006 | Cottrell et al. |
| 7,025,978 | B1 | | 4/2006 | Sirunyan et al. |
| 7,132,448 | B2 | | 11/2006 | Cottrell et al. |
| 7,345,092 | B2 | | 3/2008 | Cottrell et al. |
| 7,354,595 | B2 | | 4/2008 | Cottrell et al. |
| 7,368,435 | B2 | | 5/2008 | Cottrell et al. |
| 7,531,186 | B2 | | 5/2009 | Boeckh et al. |
| 7,855,231 | B2 | | 12/2010 | Cottrel et al. |
| 7,906,128 | B2 | | 3/2011 | Heaney et al. |
| 7,906,130 | B2 | | 3/2011 | Sabnis et al. |
| 7,906,535 | B2 | | 3/2011 | Cottrell et al. |
| 7,910,122 | B2 | | 3/2011 | Sirinyan et al. |
| 8,097,603 | B2 | | 1/2012 | Sirinyan et al. |
| 2006/0252728 | A1 | | 11/2006 | Sirinyan et al. |
| 2007/0078171 | A1 | | 4/2007 | Andersch et al. |
| 2008/0306138 | A1 | | 12/2008 | Zupan et al. |
| 2009/0069386 | A1 | | 3/2009 | Dairiki et al. |
| 2013/0130908 | A1 | * | 5/2013 | Westbye ................ A01N 25/02 504/273 |

FOREIGN PATENT DOCUMENTS

| CA | 2564234 | 11/2005 |
| EP | 1212943 | 6/2002 |
| JP | 08217606 | 8/1996 |
| WO | 2004089083 | 10/2004 |
| WO | 2005007140 | 1/2005 |
| WO | 2006027124 | 3/2006 |
| WO | 2006027125 | 3/2006 |
| WO | 2006027126 | 3/2006 |
| WO | 2006127407 | 11/2006 |
| WO | 2008030385 | 3/2008 |
| WO | 2008048963 | 4/2008 |
| WO | 2008098168 | 8/2008 |
| WO | 2010011596 | 1/2010 |
| WO | 2010059529 | 5/2010 |
| WO | 2010096623 | 8/2010 |

OTHER PUBLICATIONS

VetSTREET, Flea and Tick Prevention, Mar. 2014.*
Eurobichons, Use of shampoos in Dogs, Jun. 13, 2007.*
Stanneck D et al, Evaluation of the long-term efficacy and safety of an imidacloprid 10%/flumethrin 4.5% polymer matrix collar (Seresto) in dogs and cats naturally infested with fleas and/or ticks in multicentre clinical fields studies in Europe, Parasites & Vectors, 2012, pp. 1-11.
International Search Report mailed Apr. 6, 2014 for PCT/IB2013/059385, filed Oct. 16, 2013.
International Preliminary Report on Patentability dated Jan. 11, 2015 for PCT/IB2013/059385.
EP Search Report mailed Apr. 29, 2016 for EP13847258.4, filed May 12, 2015.

* cited by examiner

*Primary Examiner* — Jean Cornet
(74) *Attorney, Agent, or Firm* — A.C. Entis-IP Ltd.

(57) ABSTRACT

Embodiments of the invention relate to compositions for topical administration to dogs and cats comprising the active components dinotefuran and flumethrin, and methods for the treatment and prevention of flea and tick infestation comprising topical administration of such compositions.

20 Claims, 11 Drawing Sheets

TOPICAL FORMULATIONS FOR TREATING PARASITIC INFESTATIONS

RELATED APPLICATIONS

The present application is a US National Phase of PCT Application No. PCT/IB2013/059385, filed on Oct. 16, 2013, which claims the benefit under 35 U.S.C. §119(e) of U.S. Provisional 61/714,242 filed on Oct. 16, 2012, and U.S. Provisional 61/841,429 filed on Jul. 1, 2013 the disclosure of which is incorporated herein by reference.

TECHNICAL FIELD

Embodiments of the invention relate to topical formulations for treating parasitic infestations of mammals, and in particular, dogs and cats.

BACKGROUND

Dogs, cats and other household pets may become infested by ectoparasites (surface dwelling parasites) known as fleas and ticks. Common fleas which affect pets include the cat flea (*Ctenocephalides felis*) and the dog flea (*Ctenocephalides canis*). Fleas tend to feed on the blood of pets causing discomfort to the animal. Fleas may also bite humans, causing irritation and potentially causing allergic reactions.

*Rhipicephalus sanguineus*, the brown dog tick, is a tick commonly found on dogs in a household setting. It has been implicated in causing disease in dogs, including babesiosis and ehrlichiosis and in humans including Rocky Mountain spotted fever.

SUMMARY

An aspect of embodiments of the invention relates to compositions for topical administration to dogs or cats comprising active components dinotefuran and flumethrin. Dinotefuran and flumethrin are known by the chemical names 2-Methyl-1-nitro-3-(tetrahydrofuran-3-ylmethyl) guanidine and cyano (4-fluoro-3-phenoxyphenyl) methyl 3-[2-chloro-2-(4-chlorophenyl)ethenyl]-2,2-dimethyl cyclopropane carboxylate respectively. Compositions according to embodiments of the invention have proven to be effective in curing and preventing flea and tick infestation in dogs. These compositions have improved characteristics relative to previously known compositions including: sustained activity against both fleas and ticks, no irritation to treated animals and long lasting effect even after treated animals are bathed.

In an embodiment of the invention, the weight ratio of dinotefuran to flumethrin in the composition is from about 4:1 to about 1:1. In an embodiment of the invention, the weight ratio of dinotefuran to flumethrin is about 3:1. These compositions were found to be effective in treating dogs.

In an embodiment of the invention, the weight ratio of dinotefuran to flumethrin in the composition is from about 40:1 to about 10:1. In an embodiment of the invention, the weight ratio of dinotefuran to flumethrin is between about 30:1 and about 15:1. These compositions are particularly advantageous in treating cats.

Compositions according to embodiments of the invention may comprise about 5-30% dinotefuran and about 0.2%-5% flumethrin. The remainder of the compositions may comprise solvents or additional excipients.

In addition, aspects of embodiments of the invention relate to methods of treating mammals, in particular dogs and cats suffering from flea and/or tick infestation, comprising topical administration of compositions that comprise dinotefuran and flumethrin in accordance with an embodiment of the invention. In an embodiment of the invention, dinotefuran and flumethrin are administered once a month.

Topical administration of compositions according to embodiments of the invention may be accomplished by using liquid compositions such as "spot-on" compositions designed to be administered to a region of the animal such as the back of the animal's neck. Topical administration of compositions according to additional embodiments of the invention may be accomplished by using solid or semi-solid compositions such as collars comprising active pesticidal ingredients.

According to an embodiment of the invention, in topical formulations, in addition to agents which cure and prevent tick and flea infestation such as dinotefuran and flumethrin, antihistamines may be used in combination. Exemplary antihistamines include diphenhydramine, dimetindene and clemastine.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph.

DETAILED DESCRIPTION

In the detailed description below, methods of manufacture of compositions according to embodiments of the invention are described. In addition results of animal experiments on dogs which show the effects of compositions according to embodiments of the invention are described. The experiments show that compositions according to embodiments of the invention are chemically stable, long-lasting and effective in flea and tick control in dogs or in cats without causing harmful side-effects to the animals being treated.

EXAMPLE 1

Manufacture of Compositions in Accordance with Embodiments of the Invention, for Treating Flea and Tick Infestation in Dogs or in Cats Three liquid compositions, referred to as compositions 1, 2 and 3, were made by combining the solid ingredients listed in table 1 and then adding the liquid ingredients listed in the table and stirring until a clear solution was obtained. The amounts are expressed in terms of percentage by weight.

TABLE 1

| Ingredient | Function | Amount in Composition 1 | Amount in Composition 2 | Amount in Composition 3 |
| --- | --- | --- | --- | --- |
| Dinotefuran (solid) | Pesticide | 15 | 5 | 15 |
| Flumethrin (liquid) | Pesticide | 0 | 15 | 5 |
| Permethrin (solid) | Pesticide | 35 | 0 | 0 |
| Armid ® FMPC | Solvent | 49.45 | 79.45 | 79.45 |
| Ethylan 1008 (liquid) | Surfactant | 0.5 | 0.5 | 0.5 |
| BHT (butylated hydroxytoluene) (solid) | Preservative/ antioxidant | 0.05 | 0.05 | 0.05 |

Dinotefuran and flumethrin are both commercially available pesticides. The amounts in Table 1 represent amount of technical grade dinotefuran and flumethrin, having a purity of about 95% and 90% respectively. Dinotefuran, Flumethrin and Permethrin were obtained from Shanghai Agrochina International Trade Co. Ltd., Shanghai, China. BHT was obtained from Lanxess. ARMID® FMPC and Ethylan 1008 were obtained from Akzo Nobel.

The solvent blend Armid® FMPC is manufactured by Akzo Nobel (www.akzonobel.com) and is based on a blend of morpholine derivative with propylene carbonate. It is highly soluble in many other solvents such as water, propylene glycol, xylene, vegetable oil and mineral oil. Armid® FMPC is a commercially available material comprising N-formyl morpholine (80.0% by weight) and Propylene carbonate (20.0% by weight.)

Ethylan 1008 is a nonionic surfactant based on a synthetic primary alcohol, manufactured by Akzo Nobel.

Alternate solvents, surfactants and antioxidants may be used according to embodiments of the invention. For example, variations of composition 3 were made by using the solvents of isophorone, a cyclic ketone, and methylpyrrolidone instead of Armid® FMPC and solubility of dinotefuran and flumethrin was achieved.

Other combinations of N-formyl morpholine and propylene carbonate may be used as solvents in ratios other than those in Armid® FMPC such as, but not limited to, 95:5, 90:10, 75:25 and 70:30.

In addition to liquid compositions as shown in Table 1, solid compositions, comprising, for example, plastic matrices may also be formed comprising mixtures of active agents according to embodiments of the invention. In an embodiment of the invention, such a plastic matrix may be formed into a dog/cat collar, pendant or other device designed to be attached to or worn by the animal for the treatment of flea and/or tick infestation in dogs/cats.

Composition 3C is formulated in the same manner as Composition 3, with the exception that flumethrin was added in an amount of 0.8-1% by weight instead of 5% by weight, and the amount of Armid was modifed (to reach 100%.) Adult cats were administered 0.8 ml of composition 3C and kittens were administered 0.4 ml. This composition may be particularly beneficial for treatment of cats.

EXAMPLE 2A

Testing of Composition 1 on Dogs

A group of 10 medium-sized dogs of various breeds weighing between 10 and 25 kilograms (kg) each, suffering from flea and tick infestation, were subjects of a trial to test composition 1. At the start of the trial fleas and ticks on each dog were counted and then composition 1 was administered to the dog. Thereafter, fleas and ticks on each dog were again counted following 24 hours, 72 hours, 10 days, 20 days and 30 days from the beginning of the trial. In addition, observations were made as to the health and general wellbeing of the dogs including behavior; appetite; activity; and skin and hair health. Throughout the trial, the dogs were given commercial dry dog food.

Composition 1, in amount of 3.6 milliliters (ml) was administered to each dog by pouring onto the area between the shoulders and back of the neck on the first day of the trial. Fifteen days into the trial, 30 fleas and 20 ticks were added to each dog.

Figure 1A:
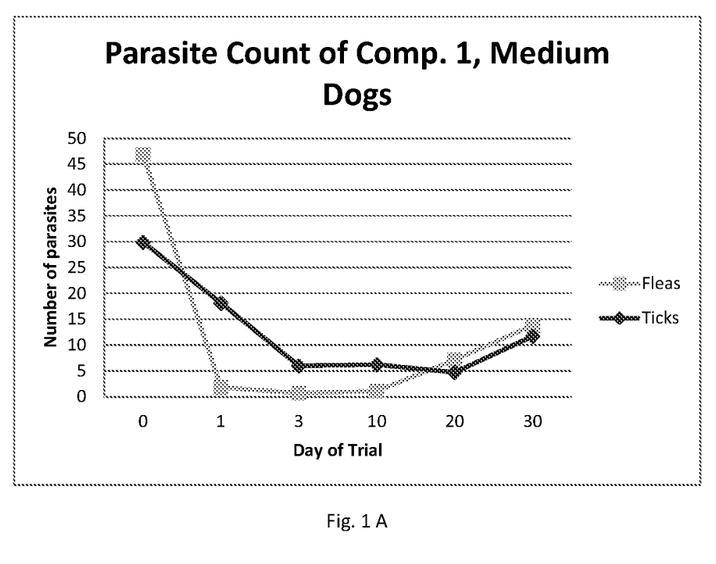
FIG. 1A shows a line graph depicting the average numbers of fleas and ticks over time on a group of medium sized dogs treated with Composition 1.

The average flea and tick count for the dogs in the trial at each parasite counting was calculated and graphed as a function of time at which the counts were made in the line graph depicted in FIG. 1A. As can be seen from the line graph, Composition 1 was effective in reducing the flea and tick count in the short term at 24 and 72 hours, but was not successful in completely eradicating fleas and ticks. In addition, at 20 and 30 days, average flea and tick count increased, indicating that a single application of composition 1 was not an effective formulation for long term flea and tick control.

The dogs were found to be in general good health throughout the trial and no external irritation or allergic reactions to the treatment were detected.

EXAMPLE 2B

Testing of Composition 2 on Dogs

A group of 10 dogs of various breeds comprising 3 small dogs (4-10 kg), 3 medium dogs (10-25 kg), and 4 large dogs (above 25 kg), suffering from flea and tick infestation, were subjects of the trial. Fleas and ticks were counted at the start of trial (before administration of the test agent) after 24 hours, 72 hours, 10 days, 20 days and 30 days. In addition, observations were made as to the health and general wellbeing of the dogs. Throughout the trial, the dogs were given commercial dry dog food.

Composition 2, in amount of 1.6 ml for small dogs, 3.6 ml for medium dogs and 4.8 ml for large dogs, was administered to each dog by pouring onto the area between the shoulders and back of the neck on the first day of the trial.

Figure 1B:
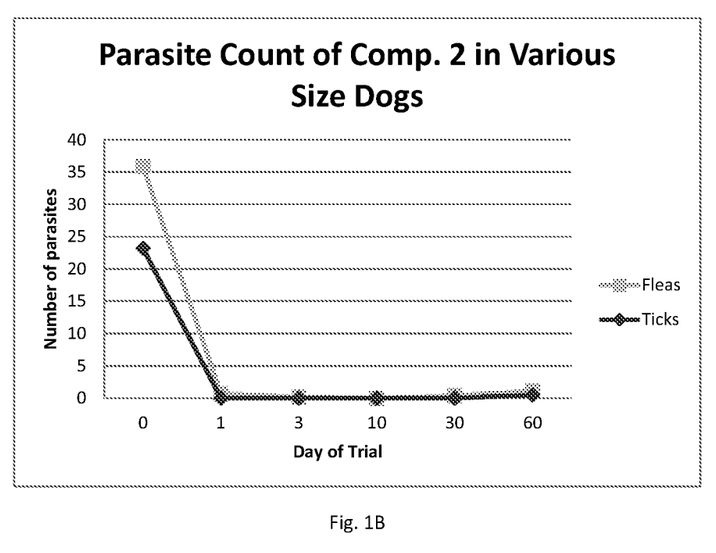
FIG. 1B shows a line graph depicting the average numbers of fleas and ticks over time on a group of various sized dogs treated with Composition 2.

The average flea and tick count for dogs at each interval of parasite counting was calculated and is tabulated in the line graph depicted in FIG. 1B. As can be seen from the line graph, Composition 2 was effective in completely eradicating fleas and ticks. In addition, even at 60 days from the start of the trial, average flea and tick count was low.

All of the dogs in the trial suffered from extreme irritation and skin reaction. In the treated dogs, dogs developed wounds on their backs from self inflicted biting which required topical treatment. Because of this adverse reaction, composition 2 is not a viable flea and tick treatment.

EXAMPLE 3

Testing of Composition 3 on Dogs

About 70 flea and tick-infested dogs were entered into the trial. The dogs were separated into groups according to table 2 having about 10 dogs in each group. The dogs were classified according to class of small, medium and large as described above in example 2B. In addition, puppies, aged 2-4 months, were tested.

TABLE 2

| Group number | Dogs (number and size/age) | Treatment |
| --- | --- | --- |
| 1 (control) | 3 small, 3 medium and 4 large | Water filled ampoule |
| 2 | 10 Puppies aged 2-4 months | 0.4 ml Comp 3 |
| 3 | 10 Small dogs | 1.6 ml Comp. 3 |
| 4 | 10 Medium dogs | 3.6 ml Comp. 3 |
| 5 | 10 Large dogs | 4.8 ml Comp. 3 |
| 6 | Bathed dogs (3 small, 3 medium, 4 large) | 1.6/3.6/4.8 ml Comp. 3 |

Group 6 dogs were bathed every 48 hours. For all groups, fleas and ticks were counted at the start of trial (before administration of the test agent) after 24 hours, 72 hours, 10 days, 20 days and 30 days. In addition, observations were made every three days as to the health and general wellbeing of the dogs, with a focus on skin health.

All of the test agents were administered to each dog by pouring the treatment composition onto the area between the shoulders and back of the neck on the first day of the trial after the first flea and tick count. Throughout the trial, the dogs were given commercial dry dog food.

Contamination with fleas and ticks occurred in all of the groups except for 2 and 6, 15 days into the trial by adding 30 fleas and 20 ticks to each dog. In group 2, the puppies were not re-contaminated with fleas or ticks. In group 6, dogs were re-contaminated with 30 ticks and 50 fleas each.

The average flea and tick count for dogs at each interval of parasite counting was calculated and is tabulated in the line graphs depicted in FIG. 2A-F.

Figure 2A:
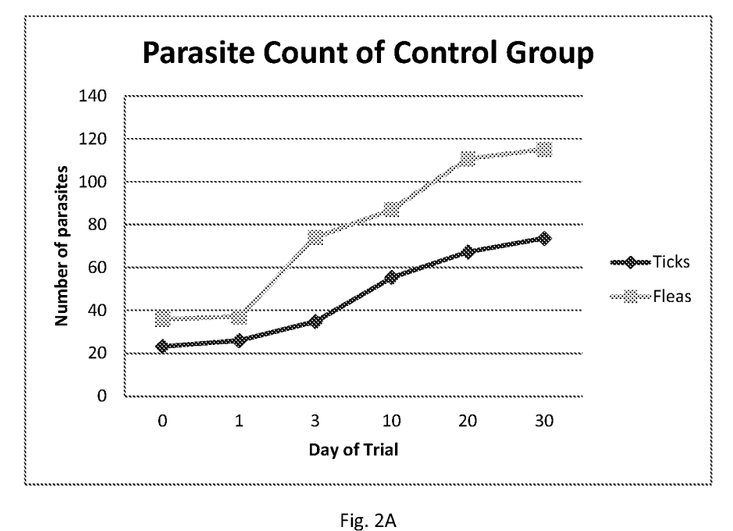
FIG. 2A shows a line graph depicting the average numbers of fleas and ticks over time on a group of dogs treated with a control comprising water.
Figure 2B:
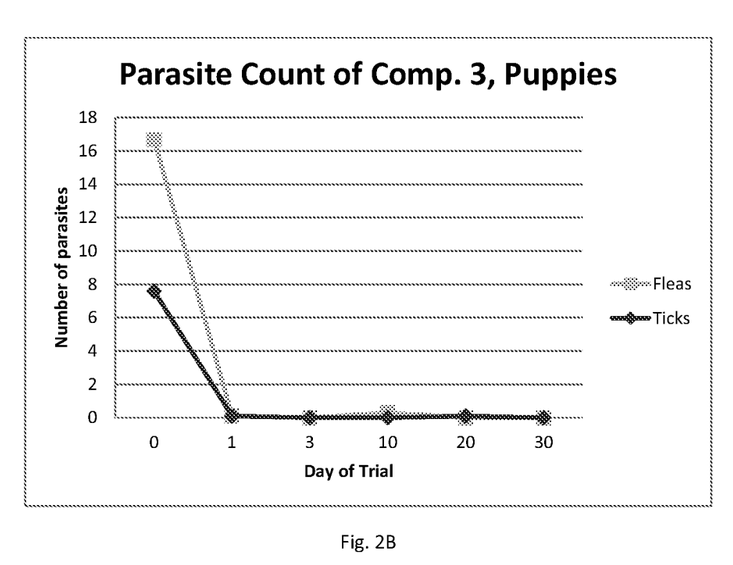
FIG. 2B shows a line graph depicting the average numbers of fleas and ticks over time on a group of puppies treated with Composition 3.
Figure 2C:
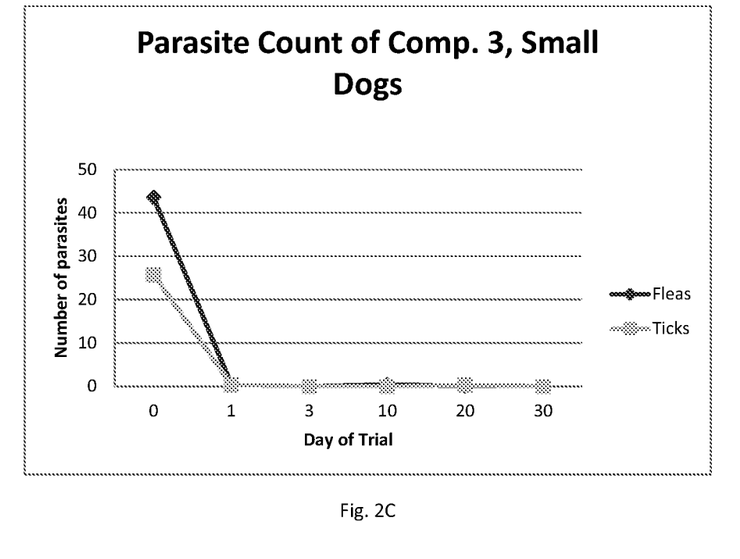
FIG. 2C shows a line graph depicting the average numbers of fleas and ticks over time on a group of small dogs treated with Composition 3.
Figure 2D:
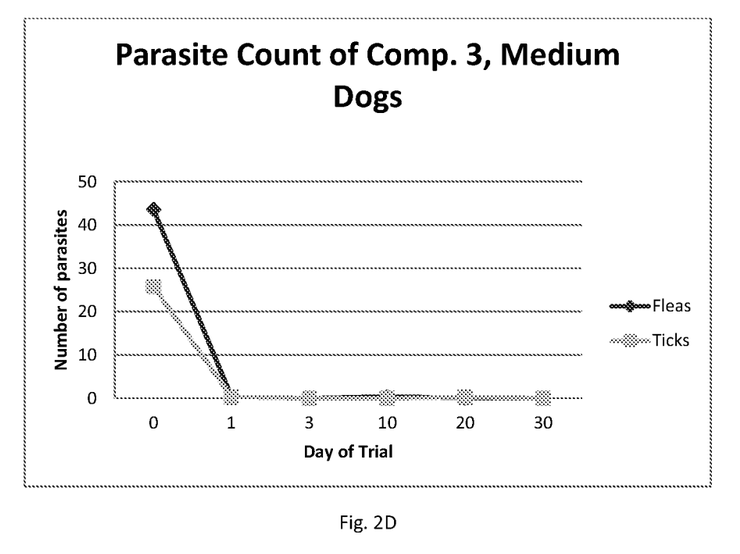
FIG. 2D shows a line graph depicting the average numbers of fleas and ticks over time on a group of medium sized dogs treated with Composition 3.
Figure 2E:
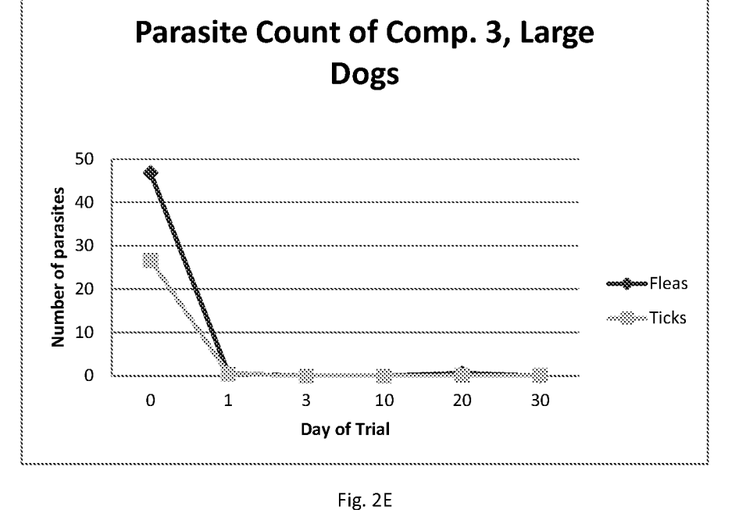
FIG. 2E shows a line graph depicting the average numbers of fleas and ticks over time on a group of large dogs treated with Composition 3.
Figure 2F:
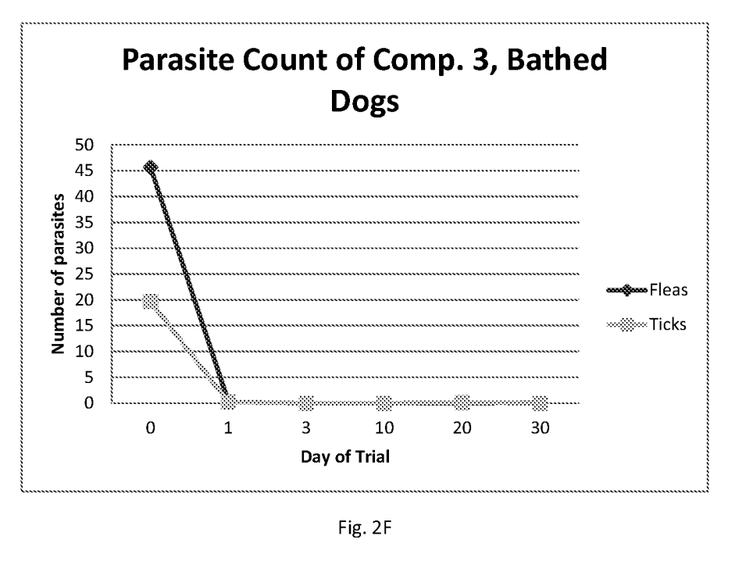
FIG. 2F shows a line graph depicting the average numbers of fleas and ticks over time on a group of various sized bathed dogs treated with Composition 3.

As can be seen from the line graph in FIG. 2A, the flea and tick count in the control group increased steadily throughout the trial. As can be seen in the line graphs in FIGS. 2B-2F, in all groups in which Composition 3 was administered, Composition 3 was effective in quickly eradicating reducing fleas and ticks in the short term at 24 and 72 hours. In addition, at the flea and tick checks after re-contamination at 20 and 30 days, average flea and tick count still remained low, indicating that Composition 3 was a long-lasting, effective composition for long term flea and tick control. As can be seen in FIG. 2F, even dogs of group 6 which were bathed frequently, remained free of ticks and fleas for the duration of the trial.

The dogs in all groups were found to be in general good health throughout the trial and no external irritation or allergic reactions to the treatment were detected in any of the dogs.

Previous attempts by the inventors to treat fleas and ticks simultaneously with one agent were not successful. For example, when the inventors applied 4.0 ml of a composition comprising 28% dinotefuran to large dogs, the composition was not effective in eliminating flea infestation after re-contamination.

Compositions according to embodiments of the invention are advantageous in that the active components act synergistically to eliminate fleas and ticks from dogs, but do not cause harmful side effects in the dogs such as skin inflammation and irritation. When used in combination, the active components do not require high quantities to retain a potent effect.

In addition, compositions according to embodiments of the invention retain efficacy and retain suitable physical characteristics for administration, for example solubility, despite the presence of two active anti-parasitic components in one composition.

In addition to compositions, methods of treatment of animals, in particular dogs, are described herein. Embodiments of the invention relate to methods of treatment dogs suffering from flea and/or tick infestation, comprising topical administration of dinotefuran and flumethrin. In an embodiment of the invention, dinotefuran and flumethrin are administered once monthly, once every 2, 3, 4, 5, 6, 7, or 8 months.

In an embodiment of the invention, dinotefuran is administered in an amount of between about 10-60 milligrams per kilogram of dog weight (mg/kg) and flumethrin is administered in an amount of between about 3-15 mg/kg. In an embodiment of the invention, dinotefuran is administered in an amount of between about 20-40 milligrams per kilogram of dog weight (mg/kg) and flumethrin is administered in an amount of between about 6-12 mg/kg. In an embodiment of the invention, dinotefuran is administered in an amount of between about 20-40 milligrams per kilogram of cat weight (mg/kg) and flumethrin is administered in an amount of between about 1-4 mg/kg.

According to an embodiment of the invention, methods of treatment of animals are performed by administering a single unit dosage form, for example, an ampoule comprising a composition comprising both dinotefuran and flumethrin. In an embodiment of the invention, the composition is a single use, plastic ampoule comprising an effective amount of composition to treat an animal for about a month.

In embodiments of the invention, methods of treatment of animals are performed by administering a composition comprising dinotefuran and another composition comprising flumethrin.

EXAMPLE 4

Manufacture of Compositions Comprising Antihistamines for Treating Dogs

Compositions were prepared in a similar way as Composition 3 in Table 1, with the modification of small amounts of antihistamines added. The amount of solvent was decreased accordingly, and all other ingredients in the compositions were added in the same proportions as in Composition 1. The amount and identity of antihistamine added is described in table 3.

TABLE 3

| Composition Number | Antihistamine | Amount |
| --- | --- | --- |
| 4 | Diphenhydramine hydrochloride | 0.5% |
| 5 | Chlorpheniramine | 1% |
| 6 | Clemastine | 0.1% |
| 7 | Certirizine | 0.5% |

Compositions 4-7 were tested at accelerated conditions, and were found to be stable in conditions simulating 24 months at room temperature.

EXAMPLE 5

Treatment of Dogs with Compositions Comprising Antihistamines

A group of 36 dogs was identified as having experienced adverse reactions to commercially available spot-on compositions including Advantix (made by Bayer Healthcare AG), Promeris (made by Pfizer), and Frontline® (made by Merial) all used according to labeled instructions. The adverse reactions included local skin irritation, discomfort and loss of hair at the place of administration.

The dogs were treated with Composition 3 (in amounts appropriate for their respective weights) and were then evaluated to determine if adverse reactions were present, at 5, 15, 30 minutes, and at 1, 2, 5, 12, 24, 48 and 96 hours after the treatment. Of the 36 dogs treated with Composition 3, four dogs experienced no adverse reactions. 23 of the dogs experienced adverse reactions similar to those experienced upon treatment with commercially available spot-on compositions. Five dogs experienced adverse reactions to a greater extent than those experienced upon treatment with commercially available spot-on compositions. Four dogs experienced adverse reactions to a lesser extent than those experienced upon treatment with commercially available spot-on compositions.

Of the 36 dogs, the 32 which experienced some adverse reactions were split into 4 groups of 8 dogs each, for treatment with Compositions 4-7. Table 4 describes the improvements in adverse reactions upon administration of the compositions comprising antihistamines:

TABLE 4

| Composition | Number of dogs with no adverse reactions | Number of dogs with alleviated adverse reactions | Number of dogs with similar adverse reactions |
| --- | --- | --- | --- |
| 4 | 5 | 3 | 0 |
| 5 | 4 | 3 | 1 |
| 6 | 2 | 5 | 1 |
| 7 | 3 | 3 | 2 |

The dogs were tested for presence of ticks and fleas and the formulations were effective in eliminating infestation. As shown in table 4, all of the anti-histamine comprising compositions were effective in eliminating or alleviating adverse effects in most of the treated dogs. From the above experiment, it seems that Composition 4 comprising diphenhydramine was the most effective in eliminating adverse effects in the treated dogs.

According to an embodiment of the invention, a topical composition is provided comprising dinotefuran and flumethrin, and an antihistamine capable of blocking histamine from binding a histamine receptor. According to an embodiment of the invention, the histamine receptor is one or a combination of more than one of: $H_1$, $H_2$, $H_3$ and $H_4$ receptors. According to an embodiment of the invention, the antihistamine is selected from the group consisting of: Acrivastine, Azelastine, Brompheniramine, Buclizine, Bromodiphenhydramine, Carbinoxamine, Cetirizine, Chlorpromazine, Cyclizine, Chlorpheniramine, Chlorodiphenhydramine, Clemastine, Cyproheptadine, Desloratadine, Dexbrompheniramine, Dexchlorpheniramine, Dimenhydrinate, Dimetindene, Diphenhydramine, Doxylamine, Ebastine, Embramine, Fexofenadine, Levocetirizine, Loratadine, Meclozine, Mirtazapine, Olopatadine, Orphenadrine, Phenindamine, Pheniramine, Phenyltoloxamine, Promethazine, Pyrilamine, Quetiapine, Rupatadine, Tripelennamine, and Triprolidine.

According to an embodiment of the invention, an antihistamine is present in a composition for treating flea and/or tick infestation in an amount of between 0.005% and 1% of the composition.

EXAMPLE 6

Compositions Comprising Reduced Amounts of Active Ingredients

Compositions 8 and 9 were prepared having ingredients as disclosed in Table 5 below Two liquid compositions, referred to as Compositions 8 and 9, were made by combining the solid ingredients listed in Table 1 and then adding the liquid ingredients listed in the table and stirring until a clear solution was obtained. The amounts are expressed in terms of percentage by weight

TABLE 5

| Ingredient | Function | Amount in Composition 8 | Amount in Composition 9 |
| --- | --- | --- | --- |
| Dinotefuran (solid) | Pesticide | 7.5 | 15 |
| Flumethrin (liquid) | Pesticide | 2.5 | 0.5 |
| Piperonyl Butoxide (liquid) | Synergist | 0 | 6 |
| Armid ® FMPC | Solvent | 89.45 | 77.9 |
| Ethylan 1008 (liquid) | Surfactant | 0.5 | 0.5 |
| BHT (butylated hydroxytoluene) (solid) | Preservative/antioxidant | 0.05 | 0.05 |

Components of the composition were obtained from sources as described in Example 1. Piperonyl butoxide is an inhibitor of cytochrome P450 enzymes and is commonly known as a synergist. The chemical name of piperonyl butoxide is 5-[2-(2-butoxyethoxy)ethoxymethyl]-6-propyl-1,3-benzodioxole. Fleas and ticks may detoxify pesticides via cytochrome P450 enzymes. Inhibitors of these enzymes may be beneficial in enhancing effects of pesticides, when used in compositions according to embodiments of the invention.

According to an embodiment of the invention, a composition, comprising between 0.01% and 20% by weight of synergist, may be prepared, according to embodiments of the invention. According to embodiments of the invention, the synergist may be an inhibitor of cytochrome P450 enzymes. According to embodiments of the invention, the synergist may be selected from the group consisting of: (2-(2-ethylhexyl)-3a,4,7,7a-tetrahydro-4,7-methano-1H-isoindole-1,3(2H)-dione (MGK 264), or S,S,S-tributyl phosphorotrithioate (DEF) or combinations of synergists.

Compositions 8 and 9 were tested at 50° C. for 3 months and for 1 week in sub zero temperatures, and the compositions were found to be stable. It is assumed that these compositions have a shelf life of at least three years at room temperatures based on the stability testing performed.

EXAMPLE 7A

Testing of Composition 8 in Dogs

About 70 flea and tick-infested dogs were entered into the trial. The dogs were separated into groups according to Table 6 having about 10 dogs in each group. The dogs were classified according to class of small, medium and large as described above in example 2B. In addition, puppies, aged 2-4 months, were tested.

TABLE 6

| Group number | Dogs (number and size/age | Treatment |
| --- | --- | --- |
| 1 (control) | 3 small, 3 medium and 4 large | Water filled ampoule |
| 2 | 10 Puppies aged 2-4 months | 0.4 ml Comp 8 |
| 3 | 10 Small dogs | 1.6 ml Comp. 8 |
| 4 | 10 Medium dogs | 3.6 ml Comp. 8 |
| 5 | 10 Large dogs | 4.8 ml Comp. 8 |
| 6 | Bathed dogs (3 small, 3 medium, 4 large) | 1.6/3.6/4.8 ml Comp. 8 |
| 7 | 3 small, 3 medium and 4 large | 1.6/3.6/4.8 ml Comp. 8 held at extreme conditions |

Group 6 dogs were bathed twice daily, starting 48 hours from the initiation of the experiment. For all groups, fleas and ticks were counted at the start of trial (before administration of the test agent) after 24 hours, 72 hours, 10 days, 20 days and 30 days. In addition, observations were made every three days as to the health and general wellbeing of the dogs, with a focus on skin health.

Group 7 dogs were administered compositions that were aged by holding at 50° C. for 3 months, simulating being held at room temperature for 3 years.

All of the test agents were administered to each dog by pouring the treatment composition onto the area between the shoulders and back of the neck on the first day of the trial after the first flea and tick count. Throughout the trial, the dogs were given commercial dry dog food.

Contamination with fleas and ticks occurred in all of the groups except for 1, 2 and 6, 15 days into the trial by adding 30 fleas and 20 ticks to each dog. In groups 1 and 2, the dogs were not re-contaminated with fleas or ticks. In group 6, dogs were re-contaminated with 30 ticks and 50 fleas each.

The average flea and tick count for dogs at each interval of parasite counting was calculated and is tabulated in the line graphs depicted in FIG. 3A-G.

Figure 3A:
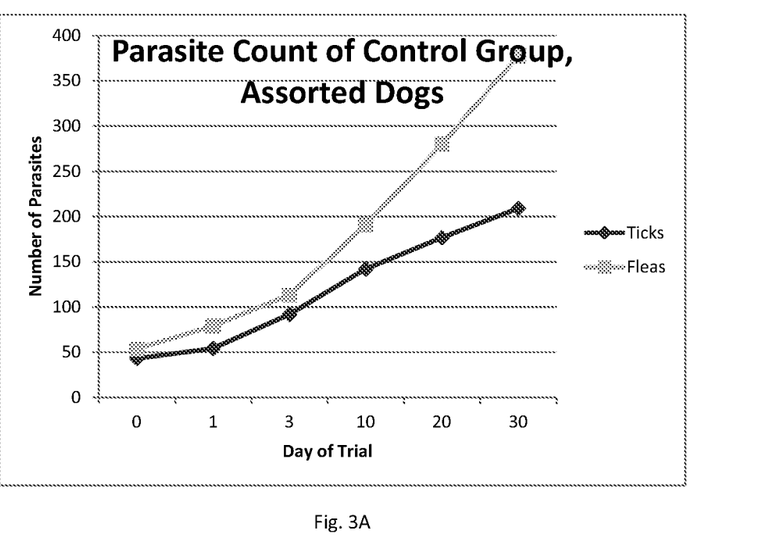
FIG. 3A shows a line graph depicting the average numbers of fleas and ticks over time on a group of dogs treated with a control comprising water.
Figure 3B:
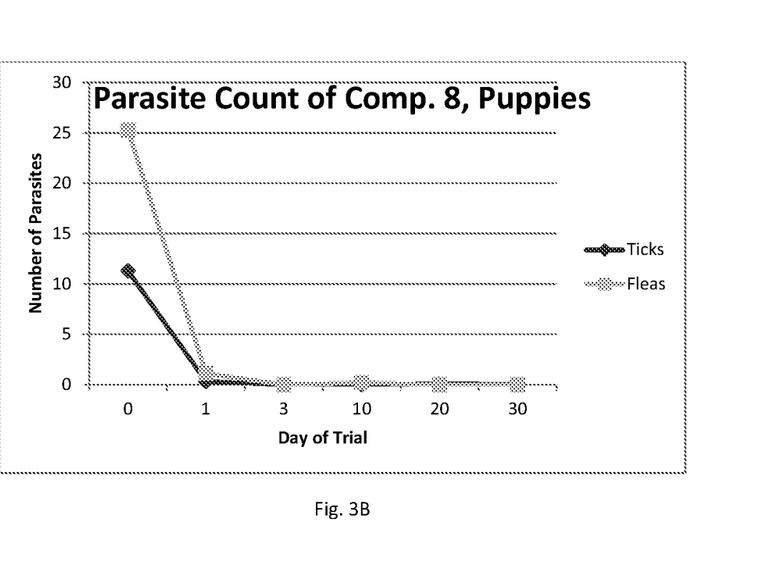
FIG. 3B shows a line graph depicting the average numbers of fleas and ticks over time on a group of puppies treated with Composition 8.
Figure 3C:
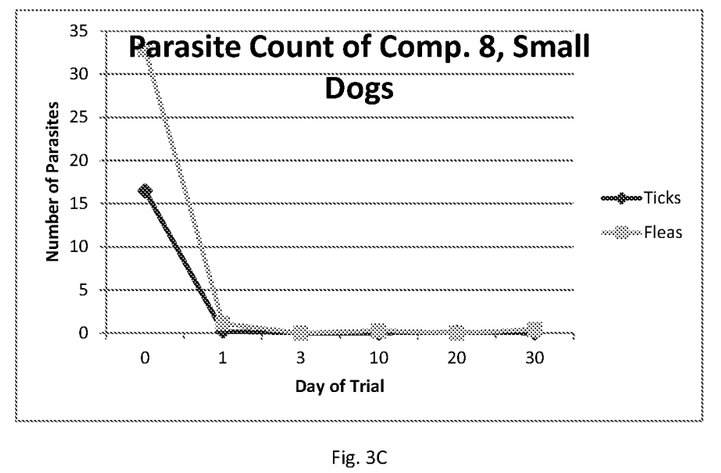
FIG. 3C shows a line graph depicting the average numbers of fleas and ticks over time on a group of small dogs treated with Composition 8.
Figure 3D:
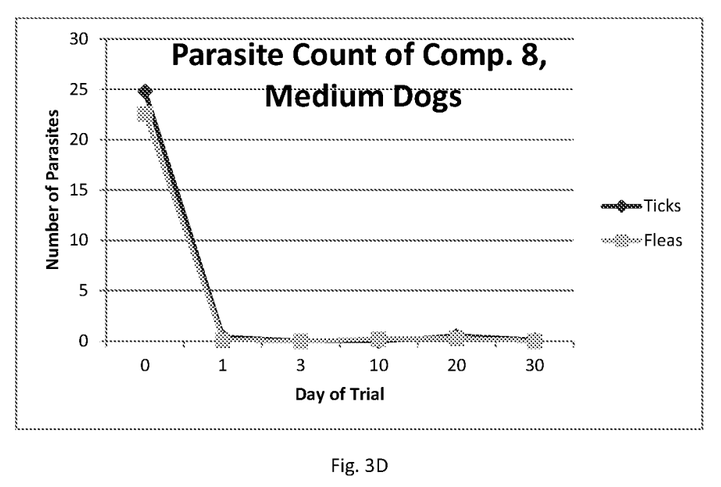
FIG. 3D shows a line graph depicting the average numbers of fleas and ticks over time on a group of medium dogs treated with Composition 8.
Figure 3E:
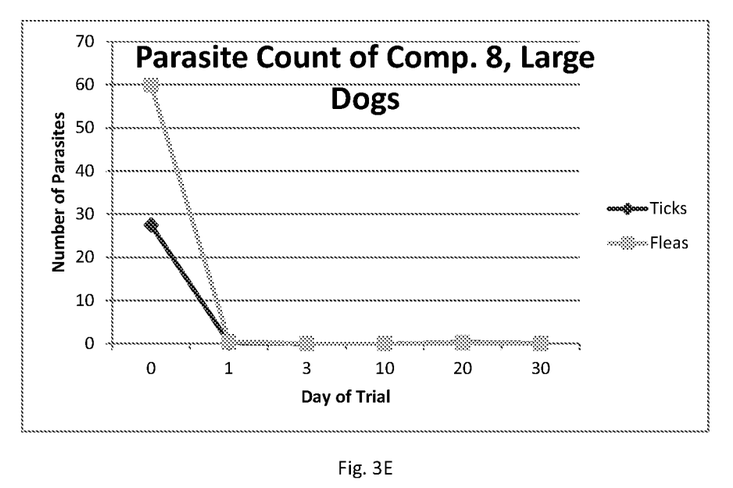
FIG. 3E shows a line graph depicting the average numbers of fleas and ticks over time on a group of large dogs treated with Composition 8.
Figure 3F:
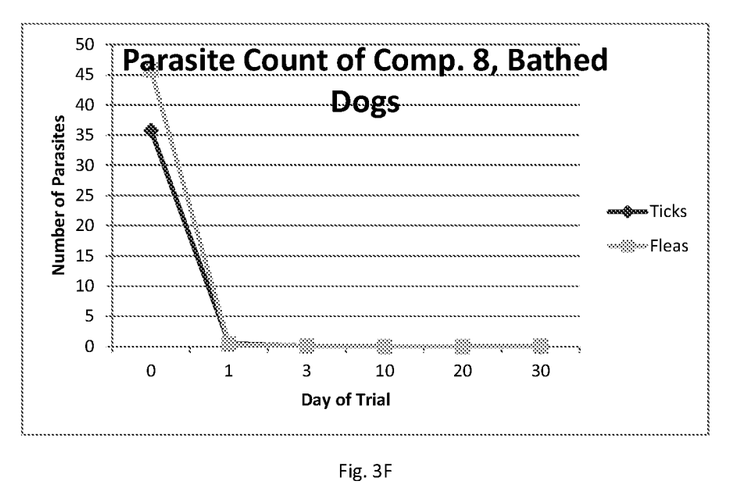
FIG. 3F shows a line graph depicting the average numbers of fleas and ticks over time on various sized bathed dogs treated with Composition 8.
Figure 3G:
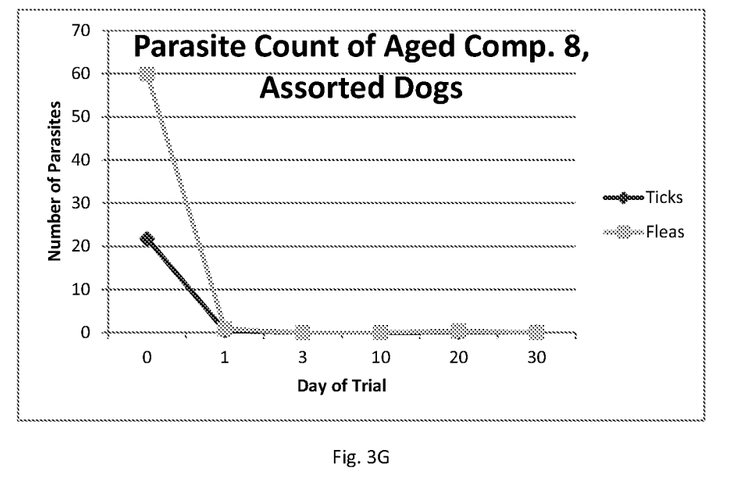
FIG. 3G shows a line graph depicting the average numbers of fleas and ticks over time on various sized dogs treated with Composition 8 which was aged after stability testing.

As can be seen from the line graph in FIG. 3A, the flea and tick count in the control group increased steadily throughout the trial. As can be seen in the line graphs in FIGS. 3B-3G, in all groups in which Composition 8 was administered, Composition 8 was effective in quickly eradicating reducing fleas and ticks in the short term at 24 and 72 hours. In addition, at the flea and tick checks after re-contamination at 20 and 30 days, average flea and tick count still remained low, indicating that Composition 8 was a long-lasting, effective composition for long term flea and tick control. As can be seen in FIG. 3F, even dogs of group 6 which were bathed frequently, remained free of ticks and fleas for the duration of the trial. FIG. 3G shows that maintaining Composition 8 at extreme temperatures of 50° C. for 3 months does not impact the safety or efficacy of the compositions in eradicating ticks and fleas. This indicates that Composition 8 may be stored for 3 years at room temperature without negative impact on its safety and efficacy in dogs.

The dogs in all groups were found to be in general good health throughout the trial and no external irritation or allergic reactions to the treatment were detected in any of the dogs.

EXAMPLE 7B

Testing of Composition 9 in Cats

About 60 flea and tick-infested cats were entered into the trial. The cats were separated into groups according to table 7 having about 10 cats in each group. The cats were classified according to class of kittens, small cats, large cats and old cats. Kittens and small cats were under 4 kg in weight. Large cats and old cats were above 4 kg in weight. Old cats were cats older than 10 years old.

TABLE 7

| Group number | Cats (number and size/age) | Treatment |
| --- | --- | --- |
| 1 (control) | 5 small and 5 large | Water filled ampoule |
| 2 | 10 Kittens | 0.4 ml Comp. 9 |
| 3 | 10 Small Cats | 0.4 ml Comp. 9 |
| 4 | 10 Large Cats | 0.8 ml Comp. 9 |
| 5 | 10 Old Cats | 0.8 ml Comp. 9 |
| 6 | 5 small and 5 large | 0.4/0.8 ml Comp. 9, held at extreme conditions |

For all groups, fleas and ticks were counted at the start of trial (before administration of the test agent) after 24 hours, 72 hours, 10 days, 20 days and 30 days. In addition, observations were made every three days as to the health and general wellbeing of the cats, with a focus on skin health.

Group 6 cats were administered Composition 9 that was aged by storing at 50° C. for 3 months, simulating being held at room temperature for 3 years.

All of the test agents were administered to each cat by pouring the treatment composition onto the area between the shoulders and back of the neck on the first day of the trial after the first flea and tick count. Throughout the trial, the cats were given commercial dry cat food.

Contamination with fleas and ticks occurred in all of the groups except for 1, 2 and 6, 15 days into the trial by adding 30 fleas and 20 ticks to each cat. In groups 1 and 2, the cats were not re-contaminated with fleas or ticks. In group 6, cats were re-contaminated with 15 ticks and 30 fleas each.

The average flea and tick count for dogs at each interval of parasite counting was calculated and is tabulated in the line graphs depicted in FIG. 4A-F.

Figure 4A:
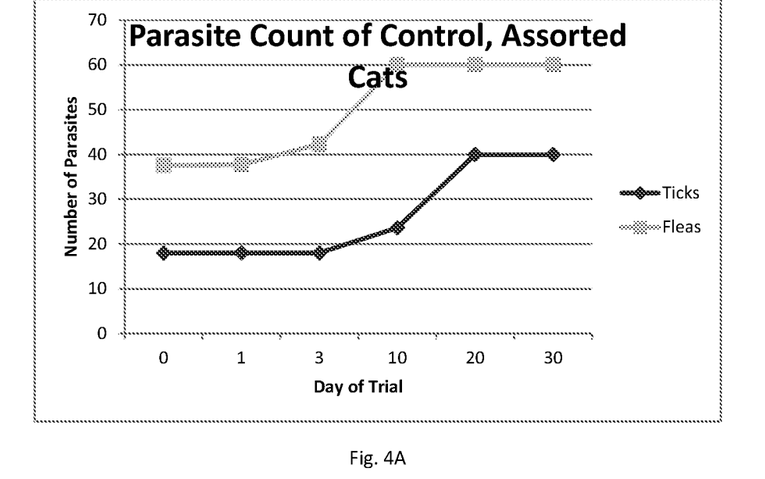
FIG. 4A shows a line graph depicting the average numbers of fleas and ticks over time on a group of cats treated with a control comprising water.
Figure 4B:
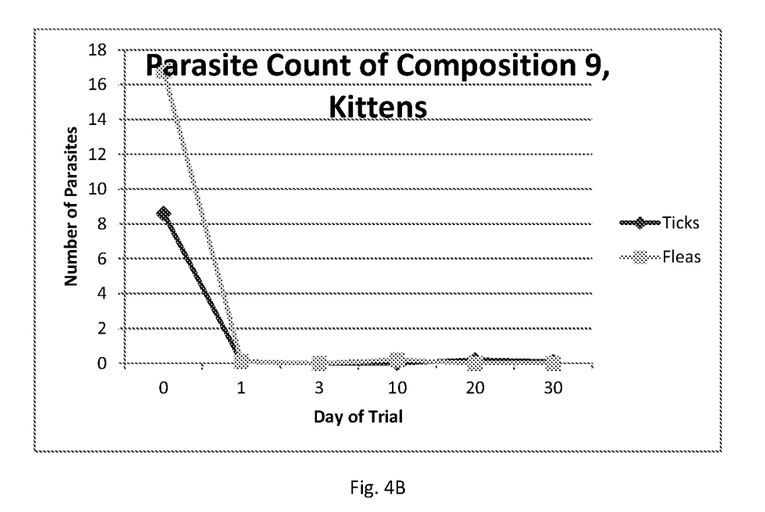
FIG. 4B shows a line graph depicting the average numbers of fleas and ticks over time on a group of kittens treated with Composition 9.
Figure 4C:
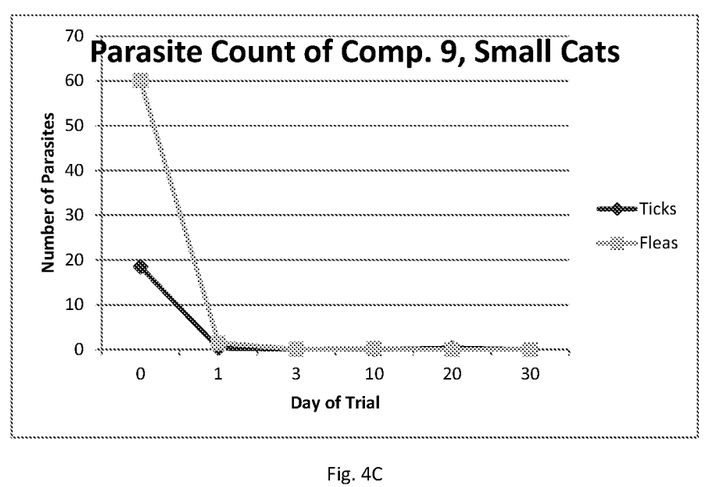
FIG. 4C shows a line graph depicting the average numbers of fleas and ticks over time on a group of small cats treated with Composition 9.
Figure 4D:
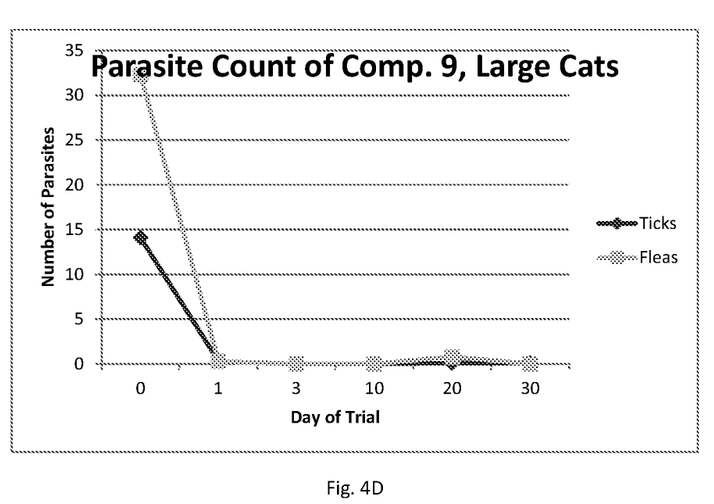
FIG. 4D shows a line graph depicting the average numbers of fleas and ticks over time on a group of large cats treated with Composition 9.
Figure 4E:
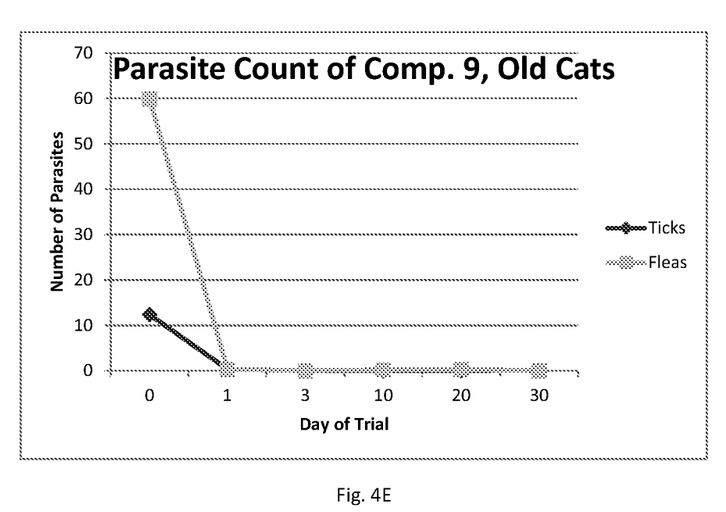
FIG. 4E shows a line graph depicting the average numbers of fleas and ticks over time on a group of old cats, older than 10 years old treated with Composition 9.
Figure 4F:
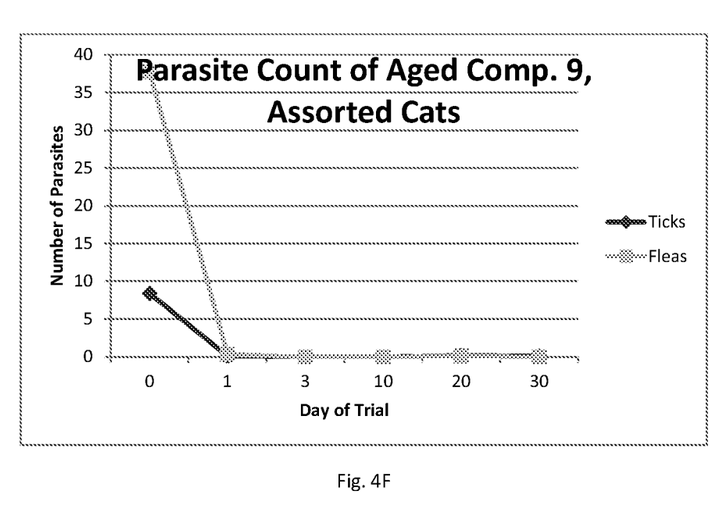
FIG. 4F shows a line graph depicting the average numbers of fleas and ticks over time on a group of various sized cats treated with Composition 9 which was aged after stability testing.

As can be seen from the line graph in FIG. 4A, the flea and tick count in the control group increased steadily throughout the trial. As can be seen in the line graphs in FIGS. 4B-4F, in all groups in which Composition 9 was administered, Composition 9 was effective in quickly eradicating reducing fleas and ticks in the short term at 24 and 72 hours. In addition, at the flea and tick checks after re-contamination at 20 and 30 days, average flea and tick count still remained low, indicating that Composition 9 was a long-lasting, effective composition for long term flea and tick control. FIG. 4E shows an effect in cats weighing more than 4 kg and more than 1 year old). FIG. 4F shows that maintaining Composition 9 at extreme temperatures of 50° C. for 3 months does not impact the safety or efficacy of the compositions in eradicating ticks and fleas. This indicates that Composition 9 may be stored for 3 years at room temperature without negative impact on its safety and efficacy in cats.

The cats in all groups were found to be in general good health throughout the trial and no external irritation or allergic reactions to the treatment were detected in any of the cats.

EXAMPLE 8

Collar Compositions

Collar compositions according to embodiments of the invention can be made of polymers which slowly and consistently release pesticides over time. Pesticides described above, combined in ratios described herein may be combined and administered to animals, such as cats and dogs in the form of a collar which slowly releases the pesticide over the course of a month to about 8 months.

Collars according to embodiments of the invention may be prepared by admixing active and inactive ingredients, extruding the mixture through an extruder, granulating the mixture and then injecting the mixture into a mold in the shape of a collar designed to be attached to an animal, for example, around the neck of an animal. Alternatively, an extruder may be used to form a collar-shaped band which may then be attached to the neck of an animal.

Preferably, liquid ingredients may be added to a porous polymer or a fraction of the porous polymer, until the liquid ingredients are absorbed. The remainder of the solid structural polymeric ingredients may then be added. Extrusion and injection may be performed at about 120-160° C.

Alternatively, liquid and powder ingredients may be dissolved and absorbed either in a porous polymer or an additional material, then other ingredients (such as structural polymer) may be added.

Alternatively, all ingredients, including liquid ingredients, may be mixed together and extruded together in an extruder or compounding matching.

Alternatively, ingredients may be fed by separate feeders to a compounding machine where they undergo granulation, followed by extrusion or injection.

Compositions according to embodiments of the invention may be formed using the following ingredients, in the following amounts ranges, or in the following specific amounts, as described in table 8 below.

TABLE 8

| Ingredient | Type/Function | Amount ranges (weight percent relative to total collar weight) | Amount used in synthetic example (weight percent relative to total collar weight) |
| --- | --- | --- | --- |
| Dinotefuran | Pesticide (active ingredient) | 5-20 | 7.5 |
| Flumethrin | Pesticide (active ingredient) | 1-10 | 2.5 |
| Piperonyl Butoxide | Synergist (active ingredient) | 0-20 | 0 |
| Paraffin oil | Oil (skin penetration enhancer) | 0-20 | 4 |
| Geranium Oil | Essential oil (Odor control) | 0-10 | 0.75 |
| Lavender Oil | Essential oil (Odor control) | 0-10 | 0.75 |

TABLE 8-continued

| Ingredient | Type/Function | Amount ranges (weight percent relative to total collar weight) | Amount used in synthetic example (weight percent relative to total collar weight) |
|---|---|---|---|
| EVA | Porous Polymer | 0-50 | 10 |
| Mixture of LLDPE and LDPE | Structural Polymer | Remainder, up to 100 | 72.5 |
|  | Antioxidant | 0-0.4 | 0 |
|  | UV stabilizer | 0-0.4 | 0 |
|  | Pigment | 0-10 | 2 |

Pesticides may be added in ratios as described in liquid formulations for dogs or for cats. A synergist may be included as disclosed above. An oil, for example paraffin oil, may be included to enhance penetration of a pesticide into an animal's skin. Essentially oils, for example, but not limited to geranium oil or lavender oil may be incorporated to reduce odors associated with other active or inactive ingredients.

Structural polymers may comprise linear low density polyethylene (LLDPE) or low density polyethylene (LDPE) or other similar polymer suitable for injection molding and adapted for slow release of pesticides over time.

A porous polymer may be used in combination with structural polymers to absorb liquid ingredients during the manufacturing process.

An antioxidant, for example, a phenolic antioxidant may be used according to embodiment of the invention to enhance the stability of the produced plastic.

A UV stabilizer may be included according to embodiments of the invention to prevent damage to the plastic by UV light.

A pigment suitable for use in polymers may be incorporated into the plastic according to embodiment of the invention.

There is further provided in accordance with an embodiment of the invention a composition for treatment and prevention of flea and tick infestation in a dog or a cat comprising an effective amount of dinotefuran and flumethrin. Optionally, the ratio of dinotefuran to flumethrin is between about 4:1 and about 2:1. Optionally, the ratio of dinotefuran to flumethrin is about 3:1. Optionally, the ratio of dinotefuran to flumethrin is between about 40:1 and about 10:1. Optionally, the ratio of dinotefuran to flumethrin is about 30:1. Optionally, the ratio of dinotefuran to flumethrin is about 15:1. Optionally, the composition further comprises an antihistamine. Optionally, the antihistamine is one of, or a combination of more than one of: Acrivastine, Azelastine, Brompheniramine, Buclizine, Bromodiphenhydramine, Carbinoxamine, Cetirizine, Chlorpromazine, Cyclizine, Chlorpheniramine, Chlorodiphenhydramine, Clemastine, Cyproheptadine, Desloratadine, Dexbrompheniramine, Dexchlorpheniramine, Dimenhydrinate, Dimetindene, Diphenhydramine, Doxylamine, Ebastine, Embramine, Fexofenadine, Levocetirizine, Loratadine, Meclozine, Mirtazapine, Olopatadine, Orphenadrine, Phenindamine, Pheniramine, Phenyltoloxamine, Promethazine, Pyrilamine, Quetiapine, Rupatadine, Tripelennamine, and Triprolidine or a salt thereof. Optionally, the antihistamine is present in an amount of between about 0.1-2% of the composition. Optionally, the antihistamine is diphenhydramine. Optionally, the composition further coprises a synergist. Optionally, the synergist is piperonyl butoxide. Optionally, the synergist is present in an amount of about 1% to about 10% of the composition.

Optionally, the composition further comprises a solvent. Optionally, the solvent comprises isophorone, methylpyrrolidone, a carbonate ester or a morpholino derivative. Optionally, the carbonate ester is propylene carbonate. Optionally, the morpholino derivative is N-formyl morpholine. Optionally, the composition further comprises a surfactant.

Optionally, the composition is packaged in a unit dosage form comprising between about 0.4 ml to about 5 ml of composition. Optionally, the amount of dinotefuran is between about 5% and about 20% of the composition by weight. Optionally, the amount of dinotefuran is between about 7.5% and about 15% of the composition by weight. Optionally, the amount of synergist is between about 5% and about 10% of the composition by weight.

Optionally, the pesticidal ingredients are combined with a polymer to form a polymeric matrix configured to be worn by an animal. Optionally, the polymeric matrix is configured to be in the form of a collar. Optionally, the composition further comprises a synergist. Optionally, the composition further comprises an oil selected from the group consisting of an essential oil and a skin penetration oil. Optionally, the skin penetration oil comprises paraffin oil. Optionally, the polymeric matrix further comprises LDPE, LLDPE, EVA or a combination of any two or more thereof. Optionally, the composition further comprises an antioxidant. Optionally, the composition further comprises a UV protectant.

There is further provided in accordance with an embodiment of the invention a method for the treatment and prevention of flea and tick infestation in a dog or a cat comprising topically administering to the dog or the cat a composition comprising dinotefuran and a composition comprising flumethrin. Optionally, the dinotefuran and flumethrin are combined in one composition. Optionally, the animal being treated is a cat and the ratio between dinotefuran and flumethrin is between 40:1 and 10:1. Optionally, the ratio between dinotefuran and flumethrin is between 30:1 and 15:1. Optionally, the animal being treated is a dog and the ratio between dinotefuran and flumethrin is between 4:1 and 2:1. Optionally, the ratio between dinotefuran and flumethrin is about 3:1. Optionally, the composition is a liquid composition applied to an area of the animal about once monthly to about once every 8 months. Optionally, the composition is a solid composition attached to the animal about once monthly to about once every 8 months.

Optionally, the composition is a liquid composition applied to an area of the animal about once monthly. Optionally, the composition is a solid composition attached to the animal about once monthly. Optionally, a dog is treated with an amount of about 2-60 mg of dinotefuran per kg of bodyweight. Optionally, a cat is treated with an amount of about 2-60 mg dinotefuran per kg of bodyweight.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A composition for treatment and prevention of flea and tick infestation in a dog or a cat comprising an effective amount of dinotefuran and flumethrin, wherein the ratio of dinotefuran to flumethrin is between about 40:1 to about 2:1.

2. The composition according to claim 1 wherein the ratio of dinotefuran to flumethrin is between about 4:1 and about 2:1.

3. The composition according to claim 1 wherein the ratio of dinotefuran to flumethrin is between about 40:1 and about 10:1.

4. The composition according to claim 1 wherein the ratio of dinotefuran to flumethrin is about 30:1.

5. The composition according to claim 1 wherein the ratio of dinotefuran to flumethrin is about 15:1.

6. The composition according to claim 1 further comprising an antihistamine.

7. The composition according to claim 6 wherein the antihistamine is present in an amount of between about 0.1-2% of the composition.

8. The composition according to claim 6 wherein the antihistamine is diphenhydramine.

9. The composition according to claim 1 further comprising a synergist present in an amount of about 1% to about 10% of the composition.

10. The composition according to claim 9 where in the synergist is piperonyl butoxide.

11. The composition according to claim 1 further comprising a solvent comprising isophorone, methylpyrrolidone, a carbonate ester or a morpholino derivative.

12. The composition according to claim 11 wherein the carbonate ester is propylene carbonate.

13. The composition according to claim 11 wherein the morpholino derivative is N-formyl morpholine.

14. The composition according to claim 1 packaged in a unit dosage form comprising between about 0.4 ml to about 5 ml of composition.

15. The composition according to claim 1 wherein the amount of dinotefuran is between about 5% and about 20% of the composition by weight.

16. The composition according to claim 15 wherein the amount of dinotefuran is between about 7.5% and about 15% of the composition by weight.

17. The composition according to claim 1 wherein the pesticidal ingredients are combined with a polymer to form a polymeric matrix configured to be worn by an animal.

18. A method for the treatment and prevention of flea and tick infestation in a dog or a cat comprising topically administering to the dog or the cat the composition according to claim 1.

19. The method according to claim 18 wherein the dog is treated with an amount of about 2-60 mg of dinotefuran per kg of bodyweight.

20. The method according to claim 18 wherein the cat is treated with an amount of about 2-60 mg dinotefuran per kg of bodyweight.

* * * * *